US010913923B2

(12) United States Patent
Ye (10) Patent No.: US 10,913,923 B2
(45) Date of Patent: *Feb. 9, 2021

(54) TISSUE CELL CULTURE DEVICE (71) Applicant: CHONGQING RUNZE PHARMACEUTICAL CO., LTD., Chongqing (CN)

(72) Inventor: Lei Ye, Chongqing (CN)

(73) Assignee: Chongqing Runze Pharmaceutical Co., Ltd., Chongqing (CN)

( * ) Notice: Subject to any disclaimer, the term of this patent is extended or adjusted under 35 U.S.C. 154(b) by 269 days.

This patent is subject to a terminal disclaimer.

(21) Appl. No.: 15/752,254

(22) PCT Filed: Aug. 9, 2016

(86) PCT No.: PCT/CN2016/094170
§ 371 (c)(1),
(2) Date: Feb. 13, 2018

(87) PCT Pub. No.: WO2017/028714
PCT Pub. Date: Feb. 23, 2017

(65) Prior Publication Data
US 2019/0024032 A1    Jan. 24, 2019

(30) Foreign Application Priority Data

Aug. 18, 2015 (CN) .......................... 2015 1 0504994

(51) Int. Cl.
*C12M 3/00* (2006.01)
*C12M 1/00* (2006.01)
(Continued)

(52) U.S. Cl.
CPC ............ *C12M 21/08* (2013.01); *C12M 23/10* (2013.01); *C12M 23/20* (2013.01); *C12M 27/16* (2013.01)

(58) Field of Classification Search
CPC .................................................... C12M 25/14
See application file for complete search history.

(56) References Cited

U.S. PATENT DOCUMENTS 6,103,255 A * 8/2000 Levene ............... A61L 27/3839
424/426
2002/0153348 A1* 10/2002 Say ........................ A61B 17/72
216/56
(Continued)

FOREIGN PATENT DOCUMENTS

CN    101212990 A    7/2008
CN    101245313 A    8/2008
(Continued)

OTHER PUBLICATIONS

English language machine translation of CN104358047, pp. 1-21, accessed Jan. 6, 2020. (Year: 2020) (Year: 2020).*
(Continued)

*Primary Examiner* — William H. Beisner
(74) *Attorney, Agent, or Firm* — Reinhart Boerner Van Deuren P.C.

(57) ABSTRACT

The present invention relates to a tissue cell culture device which includes a tissue cell culture body. The porous material used as the tissue cell culture body is a porous metallic material which is formed by pore cavities classified by a pore size of the material and cavity walls surrounding to form the classified pore cavities. The cavity wall surrounding to form an upper level of large pore cavity is provided with a lower level of small pore cavity. The pore cavities in the same level are in communication with each other. The pore cavities in different levels are also in communication with each other. This device is particularly beneficial for cell cultivation and allows tissue cells to grow freely and normally in a three-dimensional space.

6 Claims, 6 Drawing Sheets

(51) Int. Cl.
    *C12M 1/22*     (2006.01)
    *C12M 3/06*     (2006.01)

(56) References Cited

U.S. PATENT DOCUMENTS

| | | | | |
|---|---|---|---|---|
| 2005/0272153 | A1* | 12/2005 | Xuenong | A61L 27/20 |
| | | | | 435/395 |
| 2007/0275363 | A1 | 11/2007 | Bertram et al. | |
| 2018/0237733 | A1* | 8/2018 | Ye | C12M 25/14 |
| 2019/0024031 | A1* | 1/2019 | Ye | C12M 27/16 |

FOREIGN PATENT DOCUMENTS

| | | | |
|---|---|---|---|
| CN | 102630240 | A | 8/2012 |
| CN | 102864119 | A | 1/2013 |
| CN | 102864119 | B | 12/2013 |
| CN | 104368047 | A | 2/2015 |
| JP | 2004229962 | A | 8/2004 |
| WO | 2005085429 | A1 | 9/2005 |
| WO | 2007095192 | A2 | 8/2007 |

OTHER PUBLICATIONS

English language machine translation of JP2004229962, pp. 1-9, accessed on Jan. 6, 2020. (Year: 2020) (Year: 2020).*
Chen et al. "Preparation and characterization of a novel porous titanium scaffold with 3D hierarchical porous structures." J Mater Sci: Mater Med (2011) 22:839-844. (Year: 2011).*
Chen Yuejun, Preparation and Performance Research of Three-Dimensional Multi- Level Porous Titanium Implant, China Doctoral Dissertation Full Text Database, Feb. 15, 2011, Abstract, pp. 27-35, pp. 40-41 and pp. 54-64 of the main body, 110 pages.

* cited by examiner

TISSUE CELL CULTURE DEVICE

CROSS REFERENCE TO RELATED APPLICATIONS

This application is the national phase entry of International Application PCT/CN2016/094170, filed on Aug. 9, 2016, which is based upon and claims priority to Chinese Patent Application No. 201510504994.5, filed on Aug. 18, 2015, the entire contents of which are incorporated herein by reference.

TECHNICAL FIELD

The present invention relates to a tissue cell culture device, and more particularly to a tissue cell culture device which beneficially allows cells to grow freely and normally in a three-dimensional space in a culture environment.

BACKGROUND

Tissue cell cultivation is a useful and widely used technology in the fields of drug development, cell biology, toxicology, bioengineering, and tissue engineering. Tissue cell culture device generally includes a culture container (such as a culture flask, a petri dish, a culture jar, etc.). During the culture, a culture medium is added into the culture container. The culture medium may be liquid (i.e. culture solution) or solid. Generally, if the cells are suspension cells, only the culture medium is required. However, if the cells are anchorage-dependent cells and only culture medium is provided in the container, the cells would grow adherently along the container wall. In the conventional cell cultivation, cell culture plate such as a 2, 4, 6, 24 or 96-well cell culture plate is further added into the culture container. The cell cultivation is performed on the cell culture plate. However, the way in which cells are cultivated on the container wall or culture plate is not similar to the way in which cells grow in vivo. In vivo, the tissue cells all grow in a three-dimensional environment. Therefore, the current cultivation of cells in a cell culture plate within two-dimensional plane is limited by the planar growth environment, so the cell viability, morphology, and growth status etc. are significantly different as compared to those in vivo. Moreover, the cells are easily exposed to the fluid shear force of the culture solution, which causes damage to the cells. Therefore, the three-dimensional cell cultivation is of great significance. The three-dimensional cell cultivation can simulate an environment which is more similar to an in-vivo situation than the two-dimensional cultivation, so it is more advantageous than the two-dimensional cultivation. Especially for animal cells, the three-dimensional cultivation is more meaningful, because most animal cells grow adherently.

In order to achieve the three-dimensional cell cultivation, researchers have designed some devices.

Chinese patent NO. 101245313A discloses "three-dimensional cell culture insert piece, the manufacturing method, the kit, and the use thereof". This patent illustrates a three-dimensional cell culture insert piece, which is made of non-degradable non-cytotoxic polymeric material. The insert piece has a defined and regular three-dimensional porous structure and consists of a single porous lamella member or a plurality of porous lamella members fixed together. The porous three-dimensional structure allows cells to adhere to both the outer surface and the inner surface of the three-dimensional structure at the same time. The porous structure allows nutrients and metabolites to be exchanged easily, thereby facilitating the cell cultivation.

Chinese patent NO. 102864119B discloses "a carrier for cell culture and preparation method thereof". This patent illustrates a three-dimensional porous graphene support, which is used as a cell carrier and placed in the cultivation pool for cell cultivation. The porous graphene support contains metal foam, which can simulate the in-vivo growth environment of the cells, such that the three-dimensional cultivation of cells is realized. Moreover, the growth status and viability of cells can be maintained so as to promote cell growth.

With a deep analysis of the prior art described above, the drawbacks are as follows. When the number of cells in the cultivation are gradually increased, the pores would be blocked, such that a physiological dead space or nutrient-rich area would be formed, thereby reducing the flow of the nutrients or metabolites, and hindering the migration and growth of cells. Moreover, the growth and distribution of cells would be uneven in the culture body, and thus the growth condition is poor.

SUMMARY OF THE INVENTION

The objective of the present invention is to overcome the drawbacks of the prior art and to provide a tissue cell culture device which beneficially allows cells to grow freely and normally in a three-dimensional space.

The inventor believes that if a cell culture device as follows is provided, the drawbacks of the prior art can be overcome, i.e., even if during the growth and reproduction process of the cells, pores of the porous culture body become smaller or blocked, as the number of cells gradually increase, the device always has the structural feature in which nutrient solution or metabolite in the porous culture body can move freely, so as to ensure the normal growth conditions of cells.

The objectives of the present invention are realized by the following technical solutions.

A tissue cell culture device comprises a tissue cell culture body, wherein a porous material used as the tissue cell culture body is a porous metallic material; the porous metallic material is formed by pore cavities classified by a pore size of the material and cavity walls surrounding to form the classified pore cavities; the cavity wall surrounding to form an upper level of large pore cavity is provided with a lower level of small pore cavity; the pore cavities in the same level are in communication with each other; and the pore cavities at different levels are also in communication with each other. With the metallic material, the tissue cell culture body is not prone to damages under vibration. An in-vivo condition can be simulated closely and easily. Also, during the cell cultivation, loading of an insert piece can be simulated, such that a high load lasting for a long time can be withstood. Since pore cavities of the porous material are classified into different levels, and the cavity wall surrounding to form the upper level of large pore cavity is provided with the lower level of small pore cavity, the tissue cell culture body allows the nutrient solution to flow therein even if the gradual increase in the number of cells makes the pore of the culture body smaller during the growth and reproduction process of the cells, and the cells are enabled to migrate freely within the tissue cell culture body, facilitating cells to grow freely and normally in a three-dimensional space.

Furthermore, the above porous metallic material is one or more items selected from the group consisting of tantalum, niobium, tantalum-niobium alloy, medical Ti and Ti alloy, medical stainless steel, medical cobalt-based alloy, and medical shape memory alloy.

In the above tissue cell culture device, when the porous metallic material used as the tissue cell culture body is classified according to the pore size of the material, at least one level of pore cavity of the porous metallic material is a nano-level pore cavity.

In the above tissue cell culture device, when the porous metallic material used as the tissue cell culture body is classified according to the pore size of the material, at least one level of pore cavity of the porous metallic material is a micron-level pore cavity.

In the above tissue cell culture device, the cavity wall of each upper level of pore cavity of the porous metallic material which is used as the tissue cell culture body is provided with a next level of small pore cavity, or the cavity wall surrounding to form the upper level of large pore cavity is provided with all lower levels of small pore cavities, or the cavity wall surrounding to form the upper level of large pore cavity is provided with any lower level of pore cavity or any combination of more than one lower level of small pore cavity.

The inventor also believes that when the pore cavities of the porous material are classified into three levels, the cavity wall surrounding to form the upper level of large pore cavity is provided with a next level of small pore cavity, or preferably, the cavity wall surrounding to form the highest level pore cavity is provided with two lower levels of pore cavities. Such classification of pore cavities is not only beneficial for the cell growth, but also convenient for preparation.

In the above tissue cell culture device, more preferably, when the pore cavities of the porous metallic material are classified into three levels, the lowest level of pore cavity of the porous metallic material is a nano-level pore cavity, and the highest level of pore cavity of the porous metallic material is a micron-level pore cavity, and the size of the middle level of pore cavity of the porous metallic material is between the pore size of the highest level and the pore size of the lowest level.

In the above tissue cell culture device, in the porous metallic material used as the tissue cell culture body, the cavity wall surrounding to form the upper level of large pore cavity is formed by filling with the lower level of small pore cavities uniformly.

In the above tissue cell culture device, preferably, the tissue cell culture body is made into a plate structure.

In the above tissue cell culture device, the thickness of the tissue cell culture body having the plate structure is not more than 20 times as the average pore size of the highest level of pore cavity of the porous material.

The above tissue cell culture device further comprises a petri dish for placing the tissue cell culture body, and the tissue cell culture body is fixed inside the petri dish.

In the above tissue cell culture device, the petri dish is fixed on a vibration bench.

The advantages of the present invention are as follows.

1. The present invention provides a tissue cell culture device which is beneficial for cells to grow freely and normally in three-dimensional space. A porous metallic material is used as a tissue cell culture body. Particularly, the pore cavities of the porous metallic material classified according to the pore size of the material and the cavity wall surrounding to form the pore cavity are designed reasonably. The pore cavities in the same level are in communication with each other, and the pore cavities in different levels are also in communication with each other, thereby creating a three-dimensional space suitable for cells to grow freely and normally. The small pore cavity is used for the transmission and the flow of nutrients or metabolites. The mutually-communicating pores on the cavity walls can ensure the flow of nutrient solution or metabolites to form a microcirculation system that can satisfy the cell growth. The large pore cavity is used for cells to adhere and stay. The cells can move freely in the three-dimensional space between large pore cavities. The culture body provided by the invention would not form physiological dead space or concentration dead space during the cell cultivation. Also, cell growth obstacle area or nutrient-rich area would not occur. Even if the number of cells increases, such that the pore cavity becomes smaller or blocked, the random invasion or infiltration of the nutrition solution or metabolites in the cell culture body would not be hindered, ensuring the smooth and normal growth of cells, complying with the law of cell growth better. Tissue cell culture body is made of metallic material, which has high strength, good toughness, preventing the tissue culture body from being damaged easily due to vibrations. Also, during the cell cultivation, loading of an insert piece can be simulated, such that a high load lasting for a long time can be withstood. Moreover, the medical metallic material has the properties of anti-decomposition and anti-corrosion and is durable.

2. In the tissue cell culture device of the present invention, the pore cavity structure of the tissue cell culture body is classified as three level structure. In particular, when the pore cavities of the lowest level are nano-level pore cavities, and the pore cavities of the highest level are micron-level pore cavities, and the pore size of the middle level of porous metallic material is between the pore size of the highest level and the pore size of the lowest level, the growth of cells can be facilitated. The size of the device is designed according to the cell size. In such a manner, the lowest level of pore cavities are used for the transmission and flow of the nutrient solution or metabolites, and the highest level of pores are used for migration and traverse of cells, and the middle level of pore cavities are used for cells to stay. Particularly, since the lowest level of pore cavity can generate a great amount of capillary force, the infiltration and flow of the culture solution and the metabolites can be facilitated, and cells can be sucked into the cell culture body. Thus, the migration of cells is facilitated in the tissue cell culture body. Moreover, due to the presence of capillary force, the growth speed of cells would be improved.

3. In the tissue culture device of the present invention, the cavity structure of the tissue cell culture body is designed in a way that the cavity wall surrounding to form the upper level of large pore cavity is uniformly formed by filling with the lower level of small pore cavity, so that the cells can be uniformly distributed, and the nutrient solution can flow at a uniform rate. Moreover, the formation of nutrient-rich areas and uneven concentration of nutrient solution can be avoided, so that cells throughout the tissue culture device can grow normally and uniformly.

4. The cell culture body uses a plate structure, so that anchorage-dependent cells may grow inside, such that cells can be prevented from being blocked on the surface. Also, it is convenient for cells to be taken out, and the culture solution can flow through the cell culture body easily.

5. The tissue cell culture body provided by the present invention is placed in a petri dish. Regarding the culture condition, an external vibration source is provided by a vibration bench, so as to perform vertical vibration, horizontal vibration, vibration rotating around the vertical axis, and combined vibration of at least two types out of the three types of vibration, thereby promoting the flowability of culture solution in the petri dish, and facilitating the uniform distribution of the concentration and various components of tissue cells.

BRIEF DESCRIPTION OF THE DRAWINGS

The present invention will be further described with reference to the drawings and embodiments.

3-1 is a front view, 3-2 is a left view, 3-3 is a top view.

DETAILED DESCRIPTION OF THE INVENTION

The specific embodiments of the present invention will be described with reference to the drawings hereinafter. The embodiments given based on the technical solutions of the present invention illustrate detailed implementation manners and specific operating procedures. However, the scope of the present invention is not limited to the following embodiments.

Figure 1:
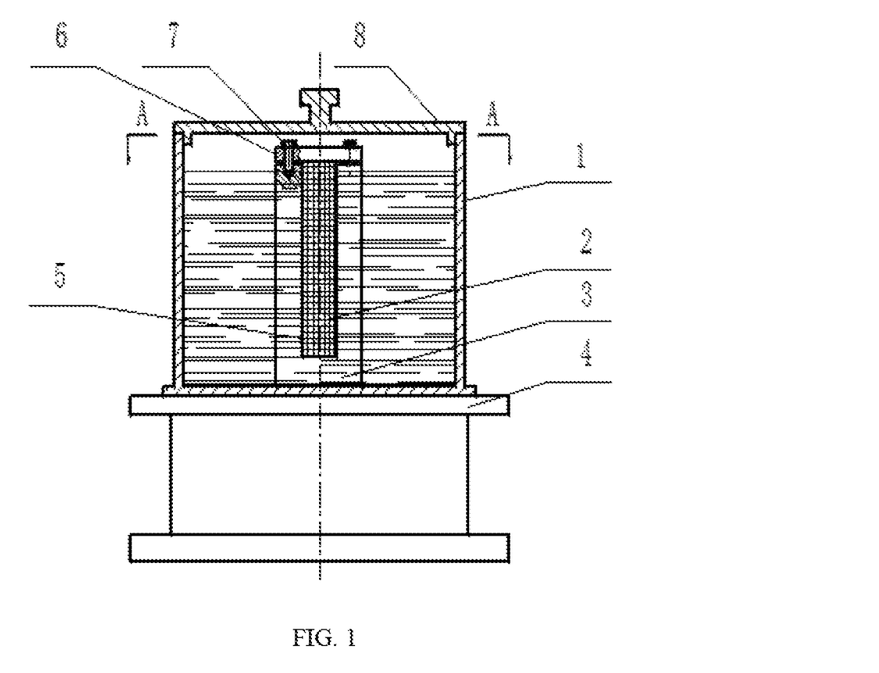
FIG. 1 is a schematic diagram of the tissue cell culture device of the present invention.
Figure 2:
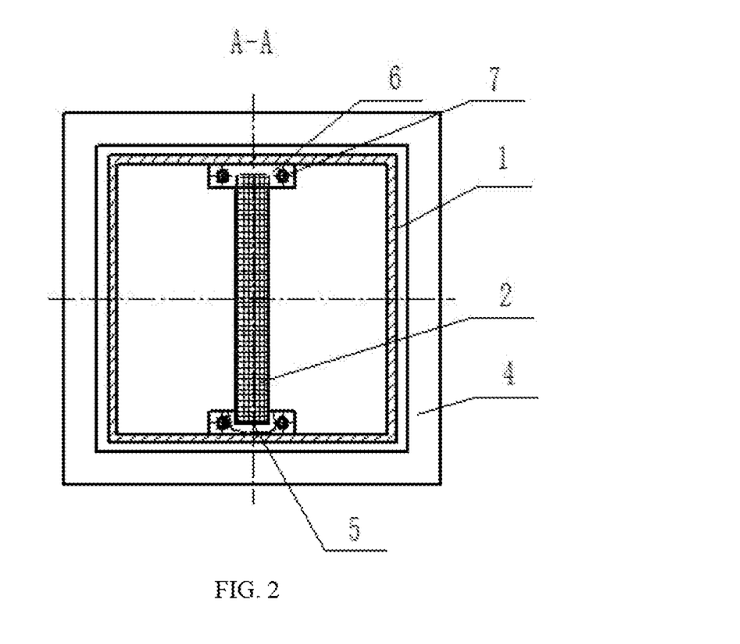
FIG. 2 is a cross-sectional view taken along A-A of FIG. 1 (the petri dish cover 8 has been removed)

As shown in FIGS. 1 and 2, 1 refers to petri dish, 2 refers to tissue cell culture body, 3 refers to fixing block for fixing the tissue cell culture body which is fixed in petri dish 1 by welding, 4 refers to vibration bench, and 5 refers to groove of fixing block 3 used for placing and fixing tissue cell culture body 2, 6 refers to press block for fixing tissue cell culture body 2, 7 refers to screw, 8 refers to petri dish cover. Tissue cell culture body 2 is disposed in the groove 5 of the fixing block 3 and is fixed to the fixed block 3 by the press block 6 and the screw 7. As such, the tissue cell culture body 2 is fixed inside the petri dish 1. The petri dish 1 can be fixed on the vibration bench 4 through commonly used fixing methods such as press plate and bolt. The petri dish cover 8 is covered on the petri dish 1.

Figure 3:
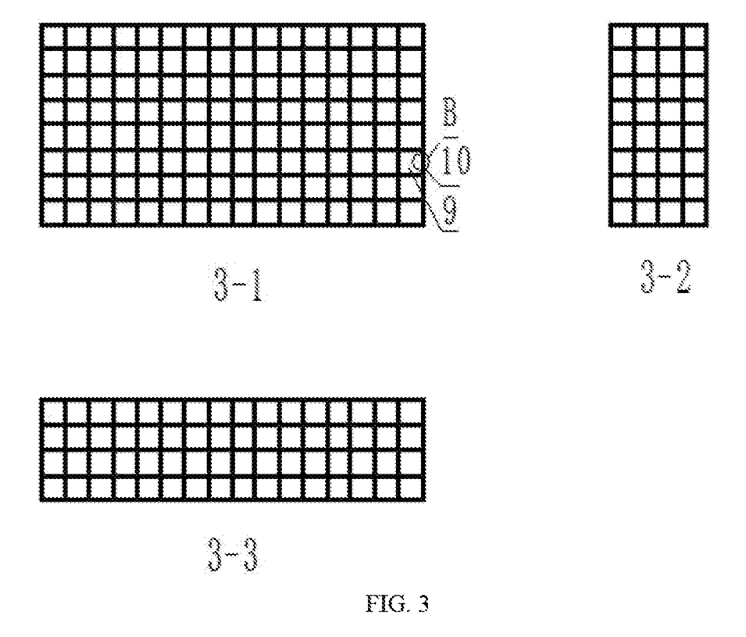
FIG. 3 is a structural schematic view of the tissue cell culture body.
Figure 4:
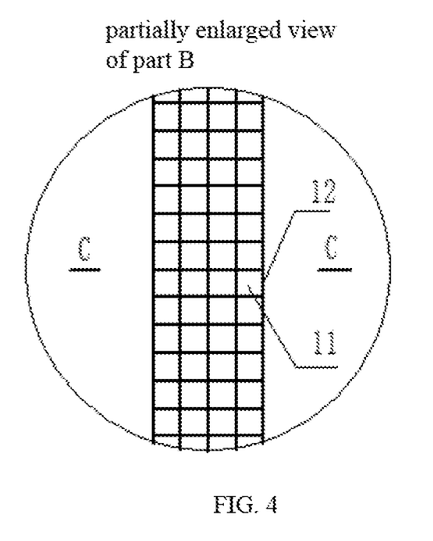
FIG. 4 is a partially enlarged view of a portion B of FIG. 3.

As shown in FIG. 3, FIG. 4 and FIG. 5, 9 refers to the highest level of pore cavity of the tissue cell culture body 2, 10 refers to the cavity wall of the pore cavity 9, and the pore cavity is communicating three-dimensionally. As shown in FIG. 4, the cavity wall 10 of the pore cavity 9 is formed by smaller pore cavity 11 (a next level of pore) and cavity wall 12 surrounding to form the pore cavity 11. With reference to the enlarged view of cavity wall 10 of FIG. 4 and cross-sectional view according to C-C of FIG. 5, the pore cavity 11 is also communicating three-dimensionally, and pore cavities of two different levels are also three-dimensionally in communication with each other.

Figure 5:
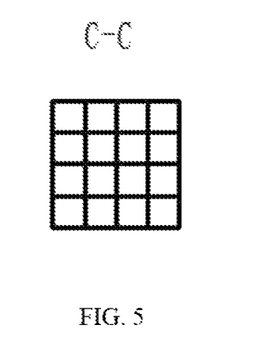
FIG. 5 is a cross-sectional view taken along C-C of FIG. 4.

Based on the illustration above, the multi-level pore structure of the tissue cell culture body with more than three levels may be formed.

During the cell cultivation, the cells are placed on the tissue cell culture body 2, and then the culture solution is added into the petri dish 1. The petri dish cover 8 covers the petri dish 1. The vibration bench 4 is activated to make the petri dish 1 vibrate. When the cultivation is accomplished, the cells on the tissue cell culture body 2 are taken out.

The detailed embodiments of the present invention are described below.

Embodiment 1

With reference to the drawings, a tissue cell culture device includes a tissue cell culture body 2, which is fixed in a petri dish 1. The petri dish 1 is further fixed on a vibration bench 4. The tissue cell culture body 2 is a porous tantalum material. The porous tantalum material is formed by pore cavities classified by a pore size of the material and cavity walls surrounding to form the respective level of pore cavities. The cavity wall surrounding to form an upper level of large pore cavity is provided with a lower level of small pore cavity. The pore cavities within the same level are in communication with each other, and the pore cavities in different levels are also in communication with each other.

Specifically, in this embodiment, the porous tantalum material has two levels of pore cavities. The cavity wall of the upper level of large pore cavity which is uniformly distributed and communicating is formed by filling with the lower level of small pore cavities which are uniformly distributed and communicating with each other. Moreover, pore cavities in two levels are in communication with each other. The pore size of the upper level of large pore cavity is 120 μm-550 μm. The pore size of the lower level of small pore cavity is 100 nm-400 nm. The tissue cell culture body 2 is a plate-shaped material, the thickness of which is 5.5 mm, which is 17 times as the average pore size of the upper level of large pore cavity.

In this embodiment, smooth muscle tissue cells are cultured. During the cultivation, the smooth muscle tissue cells are placed on the tissue cell culture body 2. MEM containing 12% of serum is added into the petri dish 1. The temperature is controlled within a range from 35-37° C. The petri dish cover 5 covers the petri dish 1. Other specific operations are the same as conventional cell culture techniques. Then the vibration bench 4 is activated to make the petri dish 1 vibrate. The vibration is in a vertical vibration mode, and the working frequency is 80 Hz. After 3 days of cultivation, the cells in the tissue cell culture body 2 are taken out and observed. Results show that the cultured cells are plump, and the growing situation is good.

In this embodiment, the porous material is prepared according to the following method.

(1) Material Preparation

Tantalum powder with a size of 1-10 μm is used as raw material, and carbamide with a particle size of 200 nm-500 nm is used as the pore-forming agent for the lowest level of pores. The starch with a size of 200 nm-500 nm is used as a binder. A slurry is prepared by volume ratio of tantalum powder:carbamide:starch:distilled water as 1:1.5:1:7.

The slurry is uniformly filled into a polyester foam having an edge diameter of 200 μm to 650 μm by a foam impregnation method to form a green body. The green body is then dried and pulverized to prepare mixed particles with a particle size of 200 pun to 650 μm, containing tantalum powder raw material, pore-forming agent, and polyester foam.

(2) The mixed particles are uniformly mixed with methyl cellulose with a particle size of 200 μm-650 μm by a volume ratio of 2:1, and then the mixture is disposed into a closed mold to be pressed into a compact green body.

(3) A vacuum sintering is performed on the compact green body. The sintered green body is processed by conventional follow-up steps according to tantalum process to obtain a porous tantalum with two levels of pore.

Embodiment 2

The tissue cell culture body 2 of the tissue cell culture device in this embodiment is made of porous 316L stainless steel which has three levels of pore cavities. The cavity wall of the first level of large pore cavities that are uniformly distributed and mutually communicating is formed by filling with the second level of and the third level of pore cavities that are uniformly distributed and mutually communicating. The pore diameter of the first level of large pore cavities is 900 μm-1500 μm. The pore diameter of the second level of pore cavities is 20 μm-40 μm. The pore diameter of the third level of pore cavities is 500 nm-800 nm. The thickness of the tissue cell culture body 2 is 18 mm, which is 15 times as the average pore size of the first level of large pore cavity. The nutrient solution is EAGLE containing 20% of calf serum. The cultured cells are epitheliumns. Other conditions are the same as those in Embodiment 1.

The vibration bench uses a vibration mode rotating around the vertical axis. The working frequency is 70 Hz. Results show that the cultured cells are plump, and the growing situation is good.

In this embodiment, the porous material is prepared by the following method.

(1) Material Preparation 316L stainless steel powder with a size of 1-10 μm is used as raw material, and carbamide with a particle size of 600 nm-900 nm is used as the pore-forming agent for the lowest level of (the third level of) pores. The ethyl cellulose with a particle size of 30 to 50 μm is used as a pore-forming agent of the second level of pores. The starch with a size of 600 nm-900 nm is used as a binder. A slurry is prepared by a volume ratio of 316L stainless steel powder:carbamide:ethyl cellulose:starch:distilled water as 1:1.5:1:1:12.

(2) The slurry is uniformly filled in a polyester foam with a pore size of 1000 μm to 1700 μm by a foam impregnation method to form a green body, which is then dried. After a vacuum sintering, porous 316L stainless steel with three levels of pore structure is obtained.

Embodiment 3

Figure 6:
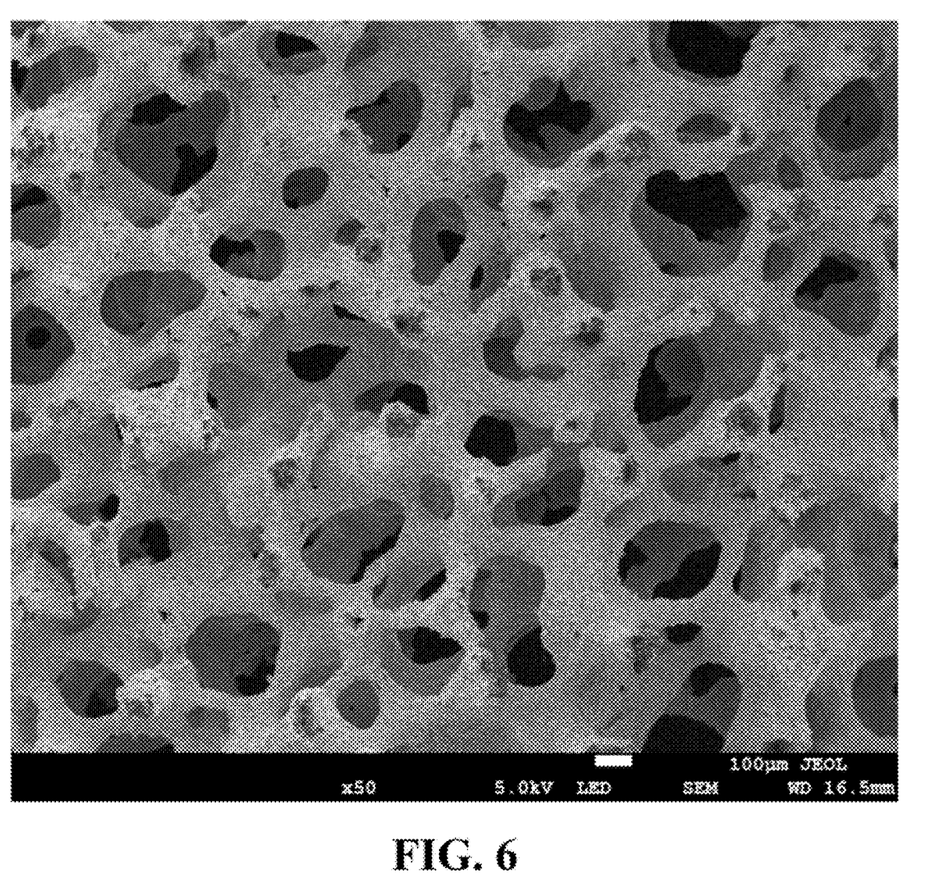
FIG. 6 is a black and white photograph showing the first level of pore cavities.
Figure 7:
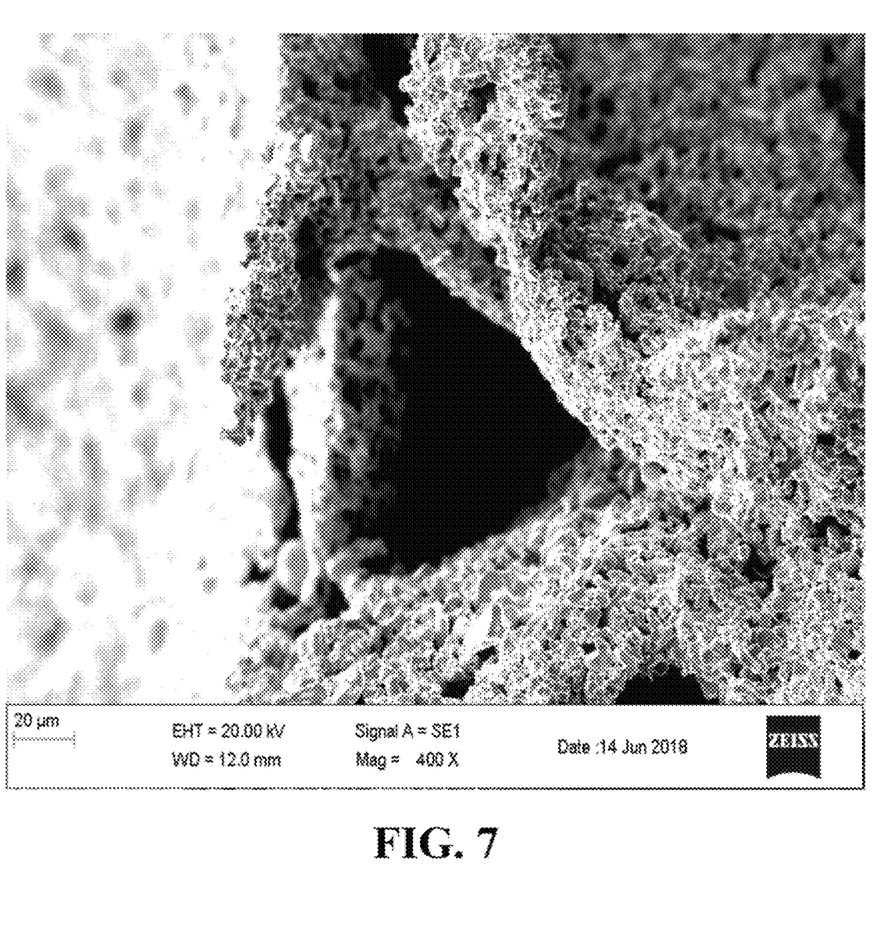
FIG. 7 is a black and white photograph showing the second level of pore cavities.
Figure 8:
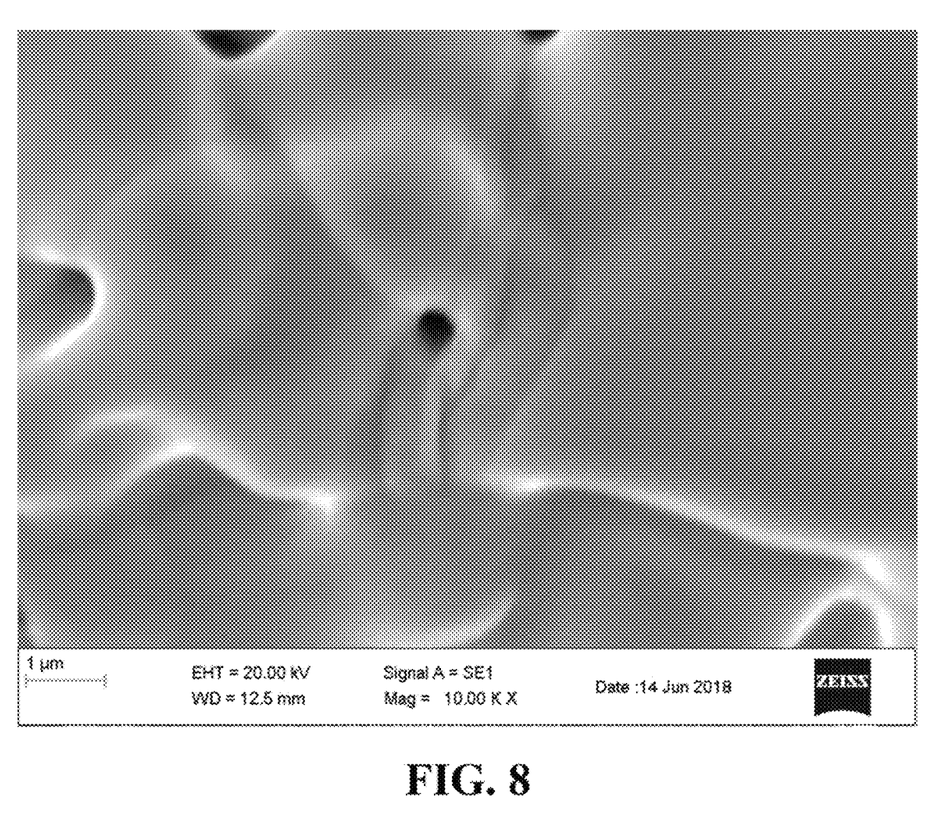
FIG. 8 is a black and white photograph showing the third level of pore cavities.

As shown in FIGS. 6-8, the tissue cell culture body 2 of the tissue cell culture device in this embodiment is made of porous niobium material which has three levels of pore cavities. The cavity wall of the highest level of pore cavities (hereinafter, referred to as the first level of pore cavity) that are uniformly distributed and mutually communicating is formed by filling with the middle level of pore cavities (hereinafter, referred to as the second level of pore cavity) that are uniformly distributed and mutually communicating. The cavity wall of the second level of pore cavities is formed by filling with the lowest level of pore cavities (hereinafter, referred to as the third level of pore cavity) which is uniformly distributed and mutually communicating. The pore cavities indifferent levels are also in communication with each other. The pore diameter of the first level of pore cavities is 200 μm-500 μm. The pore diameter of the second level of pore cavities is 40 μm-80 μm. The pore diameter of the third level of pore cavities is 150 nm 300 μm. The thickness of the tissue cell culture body 2 is 6.5 mm, which is 18 times the average pore size of the first level of pore cavity. The nutrient solution is BME containing 18% of serum. The cultured cells are bone tissue cells. Other conditions are the same as those in Embodiment 1.

The cultivation condition is in a way that a horizontal vibration and a vibration around the vertical axis of the vibration bench are performed alternately. The working frequencies are 65 Hz and 60 Hz respectively. The results of the culture show that the cells grew well.

In this embodiment, the porous material is prepared according to the following method.

(1) Material Preparation

The niobium powder with a size of 1-10 μm is used as raw material, and methyl cellulose with a particle size of 250 nm-400 nm is used as the pore-forming agent for the lowest level of pores. The polystyrene with a particle size of 250 nm-400 nm is used as a binder. A slurry is prepared by volume ratio of niobium powder:methyl cellulose:polystyrene:distilled water as 1:2:1:7.5.

The slurry is uniformly filled into a polyester foam having an edge diameter of 50 μm to 90 μm and a pore diameter of 200 μm to 300 μm by a foam impregnation method to form a green body, which is then dried and pulverized to prepare mixed particles with a particle size of 50 μm to 90 μm, containing niobium powder raw material, pore-forming agent, and polyester foam.

(2) The mixed particles are uniformly mixed with ethyl cellulose having a particle size of 50 μm-90 μm by a volume ratio of 2:1. Then, the mixture is uniformly filled into a three-dimensionally communicating polyester foam with an edge diameter of 300 μm-600 μm and a pore size of 400 μm-600 μm. After that, the polyester foam is disposed into a closed mold to be pressed into a compact green body.

(3) A vacuum sintering is performed on the compact green body. After the sintering, the green body is processed by conventional follow-up steps according to niobium process to obtain a porous tantalum with three levels of pore cavities.

Embodiment 4

The tissue cell culture body 2 of the tissue cell culture device in this embodiment is made of porous Ti6Al7Nb alloy, which has four levels of pore cavities. The cavity wall of the highest level of pore cavities (i.e. the first level of pore cavity) that are uniformly distributed and mutually communicating is formed by filling with the second level of pore cavities that are uniformly distributed and mutually communicating. The cavity wall of the second level of pore cavities is formed by filling with the third level of pore cavities and the fourth level of pore cavities that are uniformly distributed and mutually communicating. The pore cavities in different levels are also in communication with each other. The pore diameter of the first level of pore cavities is 600 μm-1100 μm. The pore diameter of the second level of pore cavities is 200 μm-400 μm. The pore diameter of the third level of pore cavities is 300 nm-600 nm. The diameter of the fourth level of pore cavities is 5 nm-150 nm. The thickness of the tissue cell culture body 2 is 17 mm, which is 16 times as the average pore size of the first level of pore cavity. The nutrient solution is DMEM containing 10% of bovine serum and high glucose with double-antibiotics.

The cultured cells are HUVEC cells. Other conditions are the same as those in Embodiment 1. The cultivation condition is in a way that a horizontal vibration and a vertical vibration of the vibration bench are performed alternately, vibrating for two minutes respectively. The working frequencies are 50 Hz and 70 Hz respectively. The results of the culture show that the cells grew well.

In this embodiment, the porous material is prepared according to the following method.

(1) The Ti6Al7Nb alloy powder with a size of 1-10 μm is used as raw material, and carbamide with a particle size of 15 nm-250 nm is used as the pore-forming agent for the lowest level of (the fourth level of) pore cavities. The ethyl cellulose with a particle size of 400 nm-700 nm is used as a pore-forming agent for the third level of pore cavities. The starch with a size of 15 nm-250 nm is used as a binder. A slurry is prepared by a volume ratio of Ti6Al7Nb alloy powder:carbamide:ethyl cellulose:starch:distilled water as 1:1.5:1:1:12.

The slurry is uniformly filled into a polyester foam having an edge diameter of 300 μm to 500 μm and a pore diameter of 400 μm to 600 μm by a foam impregnation method to form a green body, which is then dried and pulverized to obtain mixed particles with a particle size of 300 μm to 500 μm, containing Ti6Al7Nb alloy powder raw material, pore-forming agent, and polyester foam.

(2) The mixed particles are uniformly mixed with methyl cellulose having a particle size of 300 μm-500 μm by a volume ratio of 2:1 then uniformly filled into a three-dimensionally communicating polyester foam with an edge diameter of 700 μm-1200 μm and a pore size of 1600 μm-2000 μm. After that, the polyester foam is disposed into a closed mold to be pressed into a compact green body.

(3) A vacuum sintering is performed on the compact green body. After the sintering, the green body is processed by conventional follow-up steps according to Ti6Al7Nb alloy process to obtain a porous Ti6Al7Nb alloy with four levels of pores.

Embodiment 5

The tissue cell culture body 2 of the tissue cell culture device in this embodiment is made of porous CoCrWNi alloy material (F90), which has fives levels of pore cavities. The cavity wall of the highest level of pore cavities (i.e. the first level of pore cavity) that are uniformly distributed and mutually communicating is formed by filling with the second level of and the third level of pore cavities that are uniformly distributed and mutually communicating. The cavity wall of the second level of pore cavities is formed by filling with the third level of and the fourth level of pore cavities that are uniformly distributed and mutually communicating. The cavity wall of the third level of pore cavities is formed by filling with the fourth level of and the fifth level of pore cavities that are uniformly distributed and mutually communicating. The pore cavities in different levels are also in communication with each other. The pore diameter of the first level of pore cavities is 1000 μm-1400 μm. The pore diameter of the second level of pore cavities is 150 μm-270 μm. The pore diameter of the third level of pore cavities is 40 μm-90 μm. The pore diameter of the fourth level of pore cavities is 400 nm-600 nm. The pore diameter of the fifth level of pore cavities is 30 nm-150 nm. The thickness of the tissue cell culture body 2 is 22 mm, which is 18 times as the average pore size of the first level of pore cavity. The nutrient solution is DMEM containing 10% of bovine serum and high glucose with double-antibiotics. The cultured cells are HUVnEC cells. Other conditions are the same as those in Embodiment 1.

The cultivation condition is in a way that vibration bench uses a horizontal vibration mode. The working frequency is 70 Hz. The results of the culture show that the cells grew well.

In this embodiment, the porous material is prepared according to the following method.

(1) The CoCrWNi alloy powder with a size of 1-10 μm is used as raw material, and carbamide with a particle size of 50 nm-250 nm is used as the pore-forming agent for the lowest level of (the fifth level of) pore cavities. The ethyl cellulose with a particle size of 500 nm-700 nm is used as a pore-forming agent for the fourth level of pore cavities. The starch with a size of 50 nm-250 nm is used as a binder. A slurry is prepared by a volume ratio of CoCrWNi alloy powder:carbamide:ethyl cellulose:starch:distilled water as 1:1.5:1:1:12.

The slurry is uniformly filled into a polyester foam having an edge diameter of 50 μm to 100 μm and a pore diameter of 400 μm to 600 μm by a foam impregnation method to form a green body, which is then dried and pulverized to obtain mixed particles with a particle size of 50 μm to 100 μm, containing CoCrWNi alloy powder raw material, pore-forming agent, and polyester foam.

(2) The mixed particles are uniformly mixed with methyl cellulose having a particle size of 250 μm-400 μm by a volume ratio of 1:1. Then, the mixture is uniformly filled into a three-dimensionally communicating polyester foam with an edge diameter of 1100 μm-1600 μm and a pore size of 1500 μm-2000 μm. After that, the polyester foam is disposed into a closed mold to be pressed into a compact green body.

(3) A vacuum sintering is performed on the compact green body. After the sintering, the green body is processed by conventional follow-up steps according to CoCrWNi alloy process to obtain a porous CoCrWNi alloy with five levels of pores.

What is claimed is:
1. A tissue cell culture device, comprising:
  a tissue cell culture body; wherein the tissue cell culture body is formed of a porous metallic material;
  the porous metallic material is formed by pore cavities classified by a pore size of the material and cavity walls surrounding to form respective level of pore cavities;
  wherein the pore cavities of the porous metallic material are classified as three levels, in the porous metallic material, a third level of pore cavity of the porous metallic material is a nano-level pore cavity, a first level of pore cavity of the porous metallic material is a micron-level pore cavity, and a size of a second level of pore cavity of the porous metallic material is between the pore size of the first level and the pore size of the third level;
level of pore cavity is providing with the third level of pore cavity;
  the pore cavities in the same level are in communication with each other; and
  the pore cavities in different levels are also in communication with each other;
  the cavity wall surrounding to form the first level of pore cavity is provided with a second level of pore cavity, and the cavity wall surrounding to form the second level of pore cavity is provided with the third level of pore cavity;
  or the cavity wall surrounding to form the first level of pore cavity is provided with the second and third levels of pore cavities;

wherein the cavity wall surrounding to form the first level of large pore cavity of the porous metallic material is uniformly formed by filling with the second level of pore cavities, and the cavity wall surrounding to form the second level of large pore cavity of the porous metallic material is uniformly formed by filling with the third level of pore cavities;

wherein the pore diameter of the first level of pore cavities is 200 μm-500 μm, the pore diameter of the second level of pore cavities is 40 μm-80 μm, the pore diameter of the third level of pore cavities is 150 nm-300 nm.

2. The tissue cell culture device of claim 1, wherein the porous metallic material is one or more items selected from the group consisting of tantalum, niobium, tantalum-niobium alloy, medical Ti and Ti alloy, medical stainless steel, medical cobalt-based alloy, and medical shape memory alloy.

3. The tissue cell culture device of claim 1, wherein the tissue cell culture device further comprises a petri dish for placing the tissue cell culture body, and the tissue cell culture body is fixed inside the petri dish.

4. The tissue cell culture device of claim 3, wherein the tissue cell culture body is made into a plate structure.

5. The tissue cell culture device of claim 4, wherein the thickness of the tissue cell culture body having the plate structure is not more than 20 times of the average pore size of the first level of pore cavity of the porous material.

6. The tissue cell culture device of claim 3 wherein the petri dish is fixed on a vibration bench.

* * * * *